United States Patent [19]

Gohlke

[11] 4,344,999
[45] Aug. 17, 1982

[54] BREATHABLE LAMINATE

[75] Inventor: Daniel J. Gohlke, Newark, Del.

[73] Assignee: W. L. Gore & Associates, Inc., Newark, Del.

[21] Appl. No.: 142,628

[22] Filed: Apr. 22, 1980

[51] Int. Cl.³ .............................................. B32B 7/02
[52] U.S. Cl. .................................. 428/212; 2/DIG. 7; 128/132 D; 428/316.6
[58] Field of Search ............... 428/310, 315, 311, 321, 428/212, 316.6; 128/132 R, 132 D; 521/905; 2/51, DIG. 5, DIG. 7

[56] References Cited

U.S. PATENT DOCUMENTS

| 3,011,172 | 12/1961 | Tames ........................................ 2/51 |
| 3,218,649 | 11/1965 | Ricter ....................................... 2/114 |
| 3,349,285 | 10/1967 | Belkin ...................................... 317/2 |
| 3,410,266 | 11/1968 | Krzewinski et al. ........... 128/132 D |
| 3,431,911 | 3/1969 | Meisel, Jr. ............................. 428/311 |
| 3,527,654 | 9/1970 | Jones et al. ........................... 428/311 |
| 3,535,197 | 10/1970 | Fishbein et al. ..................... 428/311 |
| 3,595,235 | 7/1971 | Jespersen ............................. 128/284 |
| 3,648,692 | 3/1972 | Wheeler ............................... 428/315 |
| 3,771,525 | 11/1973 | Chapuis .......................... 128/290 R |
| 3,816,233 | 6/1974 | Powers ................................. 428/311 |
| 3,842,832 | 10/1974 | Wideman et al. .................... 428/311 |
| 3,849,238 | 11/1974 | Gould et al. ......................... 428/315 |
| 3,881,489 | 5/1975 | Hartwell .............................. 428/311 |
| 3,953,566 | 4/1976 | Gore ..................................... 264/288 |
| 3,974,308 | 8/1976 | Winters ................................ 428/311 |
| 4,187,390 | 2/1980 | Gore ..................................... 428/304 |
| 4,194,041 | 3/1980 | Gore et al. ......................... 2/DIG. 5 |
| 4,196,245 | 4/1980 | Kitson et al. ..................... 2/DIG. 7 |

Primary Examiner—William J. Van Balen
Attorney, Agent, or Firm—Mortenson & Uebler

[57] ABSTRACT

A flexible, breathable laminate is provided for use in, for example, hospital gowns and the like, or tents. The article prevents liquids such as blood, alcohol and water from penetrating through internally while at the same time permits water vapor such as perspiration to pass out externally. The article comprises an inner layer of hydrophobic material and an outer attached layer of hydrophilic material containing a solid particulate or a liquid additive. For its intended uses, the article is fabricated possessing the following favorable combination of properties when compared to prior art materials: water vapor permeability, non-glare outer surface, bacteria barrier, comfort and/or drape, non-linting, liquid resistance, sterilizability and antistatic characteristics.

11 Claims, 5 Drawing Figures

Mullins Water Entry Pressure

Bacterial Penetration

Moisture Vapor Transmission Rate

BREATHABLE LAMINATE

FIELD OF THE INVENTION

This invention relates to a synthetic article in sheet form that possesses resistance to penetration of liquids such as water, blood or alcohol, but allows passage of water vapor. The article is a bacteria barrier and has non-glare and/or antistatic surface characteristics. The article is useful in hospital gowns and the like, and in tents such as black-out tents.

BACKGROUND OF THE INVENTION

Surgical gowns, drapes and the like protect surgically prepared areas of the skin from contamination and also protect the surgeons and nurses against contamination through contact with unprepared or contaminated areas of the patient's skin. The surgical gown should present a sterile barrier to protect the patient from contamination through contact with the surgeon.

Liquid imperviousness of the gown or drape is recognized as an important property in assuring that the gown or drape presents a sterile surface and acts as a barrier to the passage of bacteria. If blood and other liquids strike through the surgical drape and contact the skin of the patient, bacteria which are deposited on the surface of the drape may be wicked through the capillary channels to the skin of the patient, and bacteria present on the skin of the patient may be wicked outward through capillary channels to the outer surface of the drape and the surgeon's gown may become contaminated by contact with the drape. In the case of the surgical gown, by a similar process, liquids may be wicked through to the skin of the surgeon.

Surgical gowns and drapes have been made from a variety of materials, nine of which will be compared hereinbelow with the laminate of this invention. Linen, muslin and other woven fabrics are common reusable materials. Nonwoven, fibrous disposable sheets are known. U.S. Pat. No. 3,410,266 discloses a laminated fabric construction in which a liquid-impervious, organic plastic film is sandwiched between liquid repellant fibrous sheets.

Fabrics and papers treated with water repellants such as silicone, fluorocarbons and other water repellants are known. Gowns constructed of plastic and waterproofed or water repellant paper are disclosed in U.S. Pat. No. 3,218,649.

In addition to being liquid repellent and a bacteria barrier, hospital gowns desirably present a non-glare outer surface, are nonlinting, possess antistatic characteristics and, not least importantly, are comfortable to the surgeon. U.S. Pat. Nos. 3,349,285 and 3,011,172 disclose elaborate means for electrically grounding gowns to render them antistatic in the potentially explosive atmosphere of an operating theatre.

Laminated materials which are waterproof and breathable and which are especially suited for use in rainwear or tents are disclosed in U.S. Pat. No. 4,194,041, assigned to the same assignee as the present application. That invention provides a layered article, for use in waterproof garments or tents, that is waterproof, resistant to surface active agents in perspiration, and that still permits the evaporation of perspiration and the transfer of moisture vapor through the layered article.

That invention comprises a combination of at least two layers: (1) an interior, continuous hydrophilic layer that readily allows water to diffuse through, prevents the transport of surface active agents and contaminating substances such as those found in perspiration, and is substantially resistant to pressure induced flow of liquid water; and (2) a hydrophobic outer layer that permits the transmission of water vapor and provides thermal insulating properties even when exposed to rain.

Garments made of those materials are permanently waterproof from exterior water sources yet allow the evaporation of perspiration whenever the partial pressure of water vapor inside the garment exceeds that outside.

The hydrophilic film used in the invention of U.S. Pat. No. 4,194,041 has a moisture vapor transmission rate exceeding 1000 gms./m$^2$. day, and preferably above about 2000 gms./m$^2$. day, permits no detectable transmission of surface active agents and preferably permits no detectable flow of liquid water at hydrostatic pressures up to 25 psig.

The hydrophobic layer used in that invention has a moisture vapor transmission rate exceeding 1000 gms./m$^2$. day and preferably exceeding 2000 gms./m$^2$. day, and an advancing water contact angle exceeding 90 degrees, and is preferably formed of a porous hydrophobic polymer.

It has been widely recognized that garments must be "breathable" to be comfortable. However, it is not necessary that air pass through the garment for it to be comfortable, only that water vapor from perspiration be transmitted from inside to outside so that undergarments do not become wet and so that the natural evaporative cooling effect can be achieved. Breathability and ability to transport interior moisture vapor to the external environment are used interchangeably in this discussion.

The transport of water through a layer can be achieved in a number of ways. Wicking is the most common when large quantities of moisture are to be transferred. Wicking materials are hydrophilic in that a drop of water placed on the surface of those materials forms an advancing water contact angle of less than 90 degrees so that they wet spontaneously. They are also porous with pores that interconnect to make complete pathways through the wicking material. Liquid water moves by capillary action from interior surface to exterior surface where it evaporates. Although some wicking materials may resist pressure induced flow of liquid water through them due to the tortuousity and length of flow path, they readily transport liquids by capillary action from the exterior surface to the interior surface and so are unsuitable for hospital gowns. The comfort attributed to cotton garments results from its ability to transport water to the exterior surface where it can readily evaporate and provide cooling. Another natural wicking material is leather which owes its great comfort to breathability via wicking.

The inventions disclosed in U.S. Pat. Nos. 3,953,566 and 4,194,041 have provided porous membranes that satisfy the two comfort requirements of being waterproof while also being permeable to the flow of water vapor. These membranes are usually laminated to fabrics for mechanical protection and style. The membranes are inherently hydrophobic and contain very small pores that resist the entry of liquid water even at substantial pressures or when rubbed or flexed, but readily allow the flow of gases, including water vapor. Unlike wicking materials, breathability is achieved by evaporation of liquid water inside the garment or on the inner surface of the membrane followed by gaseous flow or diffusion of water vapor through the membrane to the outside.

SUMMARY OF THE INVENTION

A flexible layered article suitable for use in hospital gowns and the like, or tents, is provided which article permits transfer of water vapor preventing build-up of internal moisture.

This laminated article comprises a flexible inner layer of hydrophobic polymeric material having a moisture vapor transmission rate exceeding 1000 gms./m$^2$. day and an advancing contact angle exceeding 90 degrees, and a continuous outer hydrophilic layer attached to the outer face of the inner hydrophobic layer. This hydrophilic layer has a moisture vapor transmission rate exceeding 1000 gms./m$^2$. day and contains a particulate solid or a liquid additive. Preferred solid additives are color pigments and preferred liquid additives include antistatic agents. An additional inner textile layer may be attached to the inner surface of the hydrophobic layer for strength or aesthetic reasons if desired.

The laminate of this invention has the following properties: bacterial penetration time above 1000 minutes; water entry pressure above 20 psig, moisture vapor transmission rate above 2000 gms./m$^2$. day; can be made antistatic; and can possess a non-glare outer surface.

DETAILED DESCRIPTION OF THE INVENTION WITH REFERENCE TO THE DRAWINGS

Figure 1:
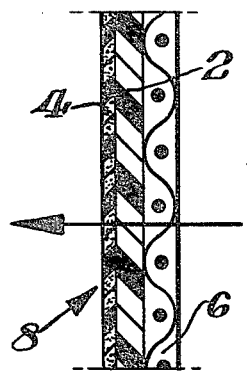
FIG. 1 is a cross-sectional view of the laminate of this invention.

A flexible, breathable laminate is provided for use in, for example, hospital gowns and the like, or tents, The article prevents liquids such as blood, alcohol and water from penetrating through internally while at the same time permits water vapor such as perspiration to pass out externally. The article comprises an inner layer of hydrophobic material and an outer attached layer of hydrophilic material containing a desired solid or liquid additive. In contrast, the laminate of the invention disclosed in U.S. Pat. No. 4,194,041 comprises an outer hydrophobic layer attached to an inner hydrophilic layer whose purpose is to block transport of surface tension lowering agents such as the oils present in perspiration. There is no mention in the reference of using the hydrophilic layer as a carrier for other additives such as solid pigment, liquid antistatic agents, and the like.

Various technical definitions are given in U.S. Pat. No. 4,194,041 concerning hydrophobic and hydrophilic materials and those definitions are incorporated herein by reference. Specifically, the term hydrophilic film used in this invention is restricted to continuous films, including closed cell foamed films, that do not allow the flow of gases or liquids through the open pore channels in the material but do transfer substantial amounts of water through the film by absorbing water on one side of the film where the water vapor concentration is high, and desorbing or evaporating it on the opposite side of the film where the water vapor concentration is low.

If a continuous film of hydrophilic material is exposed to air containing substantial water vapor on one side of the film, and to air containing less water vapor on the other side, the side of the film exposed to the higher water vapor concentration will absorb water molecules which diffuse through the film and are desorbed or evaporated on the side exposed to the lower water vapor concentration. Thus, water vapor is effectively transported through the film on a molecule by molecule basis. The hydrophilic materials of this invention do not necessarily have hydrophilic surface characteristics as indicated by advancing water contact angle. In fact, the two specific examples cited here as suitable hydrophilic materials have advancing water contact angles exceeding 90 degrees and may be considered hydrophobic from that point of view.

The hydrophilic materials of this invention are selective in absorbing and transporting water and not surface active agents and organic materials generally, nor do they allow gases such as oxygen and nitrogen to flow through them readily under hydrostatic pressure. They are also resistant to hydraulic flow of liquids, including water. These continuous, hydrophilic films are unique in transporting water solely by the absorption/evaporation mechanism. They do not transfer water by capillary action or by wicking. Water molecules are not believed to be transferred in association with other water molecules as with normal hydraulic and capillary flows. Indeed, the hydrophilic films in combination with any fabric used as a support, form a usefully waterproof sheet that possesses a moisture vapor transmission rate that is generally not greatly lower than the moisture vapor transmission rate of the fabric used as a support.

Two commercially available hydrophilic materials have been found that embody the requisite properties of this invention. One is an organic polymer with a hydrophilic backbone sold under the trademark Hypol ® by W. R. Grace and Co. Hypol ® is a reactive prepolymer that can be crosslinked by water and/or multifunctional amines, including blocked carbamate amines. Hypol ® has a backbone of polyoxyethylene units which end with toluene diisocyanate groups. The structure is essentially a branched polyether with a maximum of three reactive isocyanate (NCO) groups per molecule. The second hydrophilic material is a fluorocarbon with hydrophilic side groups sold under the trademark Nafion ® by E. I. duPont de Nemours & Co. Nafion ® is a perfluorosulfonic acid product. It is described as a copolymer of tetrafluoroethylene and a monomer such as perfluoro-3, 6-dioxa-4-methyl-7-octensulfonic acid.

Because of the great chemical difference of these hydrophilic polymers, it is believed there are additional suitable hydrophilic materials that could be useful.

To these hydrophilic polymers and prior to crosslinking is added the desired pigment in powder form which provides the needed non-glare surface of the material. Upon casting the hydrophilic film containing pigment upon the hydrophobic layer and effecting crosslinking, the laminate of this invention is produced. Other desirable ingredients such as antistatic agents can also be added. Each layer can be separately prepared and the layers attached with an adhesive.

The interior layer of the two layered embodiment of this invention is hydrophobic, porous and permeable to gases. Hydrophobic, as used here, means that water will not spread on the material and wick into its porous structure. A drop of water placed on the surface of a highly hydrophobic layer will remain in the form of a nearly spherical bead with an advancing water contact angle greater than 90 degrees.

A film of porous, expanded polytetrafluoroethylene, which has been heated above its crystalline melting point after expansion, has been found to be an ideal hydrophobic layer. These films are highly porous, a property which gives them good thermal insulating qualities, yet the pores are very small in size which leads to high water entry pressures. This porous material allows water vapor to diffuse from a zone of relatively high water vapor pressure inside a surgeon's garment to a zone of lower water vapor pressure at the cooler outside. U.S. Pat. No. 3,953,566 describes the preparation of the desirable microporous, expanded, polytetrafluoroethylene hydrophobic films. These films are commercially available from W. L. Gore & Associates, Inc., Elkton, Md., and are sold under the trademark GORE-TEX ®.

Other hydrophobic materials for use in the outer layer include highly crystalline films of expanded PTFE, which have not been heated above their crystalline melt point, and films of other microporous hydrophobic polymers such as polypropylene, which possess the necessary moisture vapor transmission and waterproofness characteristics. Celanese Plastics Co. sells such a microporous polypropylene film under the trademark Celgard ®. Other hydrophobic layers which are less useful for their insulating properties because water wets through them at lower pressures are still useful. These include tightly woven fabrics of fine, hydrophobic fibers including polyolefin fibers such as polyethylene and polypropylene, poyltetrafluoroethylene fibers, and other fibers treated with hydrophobic agents. Also, tightly spaced nonwoven webs of the above described fibers may be useful.

The hydrophilic and hydrophobic layers can be attached using a variety of procedures. Edges of the layers can be attached, for example by sewing or by an adhesive. Alternately, an adhesive can be applied to join other portions of the surface area of the two layers. This technique may reduce somewhat the area available for transmission of water vapor, but most of the area remains.

Another technique which can be used is to cast a hydrophilic layer directly on a microporous hydrophobic layer with the application of sufficient hydraulic pressure to force the hydrophilic polymer to penetrate into the surface void spaces of the hydrophobic layer and thereby bond the hydrophilic layer to the hydrophobic layer.

The novel layered article of this invention can be usefully incorporated into a variety of laminar combinations. Textile layers can be added for strength and aesthetic characteristics to both the hydrophilic layer and the hydrophobic layer. For example, in applications such as hospital gowns, it is desirable to provide an inner layer of a textile fabric, such as a polyester-cotton blend in a lightweight weave, adjacent to the inner surface of the hydrophobic layer, for strength and to provide the composite with a typical textile feel and hand. For this use, no external cloth layer is required and this is a key advantage of this invention because linting is thus eliminated.

The moisture vapor transmission rate through the layered article of the invention should be above 1000 and is preferably above 2000 gms./m$^2$. day to provide for escape of moisture from the interior of an enclosure formed by the article. These extremely high levels of moisture vapor transmission can be achieved, even when the hydrophobic layer and hydrophilic layer are adhesively bonded together over dotted portions of the area of the sheets.

The individual layers and the assembled layered article should be flexible, and preferably soft and pliable, if the article is to be used in garments such as hospital gowns or in tents. One significant advantage of the present invention is that waterproofness, bacteria imperviousness and moisture vapor transmission can be achieved in a lightweight, comfortable construction.

The laminate of this invention is illustrated schematically in cross-section in FIG. 1. Therein, the laminate 8 is shown comprising additive-containing hydrophilic layer 4 attached to hydrophobic layer 2, the layer 2 being attached to optional textile layer 6. The arrow is intended to indicate water vapor transmission through the laminate.

The laminate of this invention was tested in comparison with nine (9) other commercially available hospital gown materials. The samples are numbered for comparison purposes as follows:

1. Fiber reinforced tissue (single layer)
2. Fiber reinforced tissue (double layer)
3. Scrim reinforced tissue
4. Spunlace nonwoven
5. Spunlace nonwoven reinforced with polyethylene
6. Spunbonded polyester
7. Spunbonded polyethylene
8. Type 140 muslin
9. Tight-weave pima, quarpel treated
10. This invention The first seven (7) samples are disposables, the last three (3) are reusable.

The laminate of this invention was prepared as follows:

The hydrophilic polymer was prepared by mixing in a blender the following compounds in the proportion shown:

| Hypol ® hydrophilic polymer system: | 80.2% |
|---|---|
| Pigment: | |
| white (duPont Co., TiPure R994): | 11.4% |
| blue (Ferro Corp., V-5200): | 3.2% |
| green (Ferro Corp., V-7687): | 5.2% |

This hydrophilic polymer mixture was then applied directly to the hydrophobic layer* with the application of sufficient hydraulic pressure to force the hydrophilic polymer to penetrate into the surface void spaces of the hydrophobic layer and thereby bond the hydrophilic layer to the hydrophobic layer. The composite was heated to 175° C. to cross link the hydrophilic polymer.

*Product of W. L. Gore and Associates, Inc., Elkton, Maryland, product designation GORE-TEX ® film, expanded PTFE film of density 0.4 gm/cc, thickness 0.0375 mm, pore volume about 82%, and nominal pore size 0.2 μm.

A lightweight polyester cotton apertured tricot fabric was then attached to the hydrophobic layer side of this composite using a conventional solvent urethane adhesive and thermoplastic laminating techniques.

Finally, the hydrophilic layer of this composite was treated in a pad bath with a 2% concentration by weight in water of Nopcostat SGG11 (product of Diamond Shamrock Chemical Company) to impart antistatic characteristics.

The liquid barrier characteristics of operating room materials are usually evaluated by measuring degree of waterproofness. The above 10 samples were compared using the Mullin's Burst Test (Fed. Std. 191, Method 5512). In this test the water resistance of a material is measured by continuously increasing the pressure of water on one side of the material until either water comes through or the sample bursts.

Figure 2:
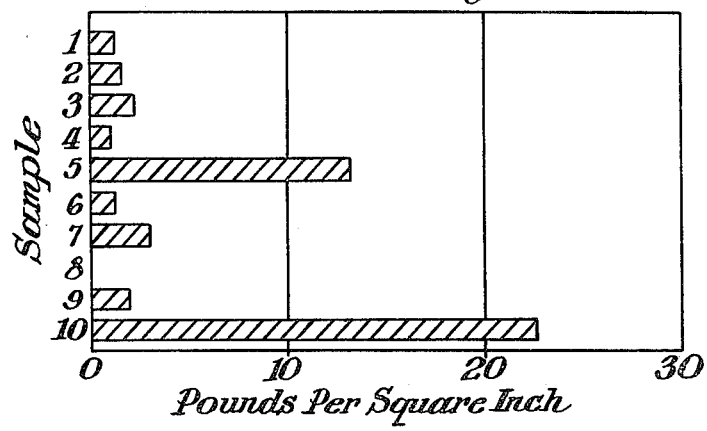
FIG. 2 is a graph showing water entry pressure data for ten different material samples including the laminate of this invention.

FIG. 2 shows the results of the water entry test for each of the materials tested. All except samples 5 and 10 failed in the 1–2 psi range. Sample 5 had the continuous, polyethylene sheet. Sample 10, the laminate of this invention, had Mullin's water entry pressure of about 22 psi.

Bacterial penetration of each of the above samples was also measured. For each test a two-chamber vessel was used, the chambers being separated by the sample to be tested. Both chambers were filled so that both sides of each sample were wetted and then the upper chamber was innoculated with psudomonis auriginosa. Samples were then taken from each lower chamber at increments of 5 and 15 minutes and at 1, 8, 24, 48 and 72 hours and tested for the presence of the bacteria.

Figure 3:
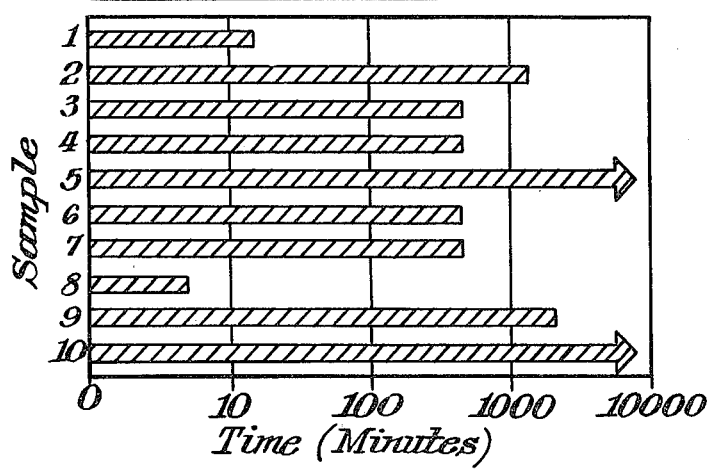
FIG. 3 is a graph showing bacterial penetration time in minutes for the same ten samples as in FIG. 2.

FIG. 3 shows the results of the bacterial penetration tests. The horizontal scale in FIG. 3 is a logarithmic scale and shows nearly a 1000-fold improvement of the best samples over the worst. As can be seen, bacteria penetrated sample 8 in less than 10 minutes. For samples 5 and 10, no bacteria were present at 72 hours and the testing was discontinued.

An important characteristic of a gown material used in the operating room theatre is comfort to the surgeon. Many materials are impervious to bacteria but are unsuitable to wear in a working environment. Measuring comfort of a material is a difficult task since it involves not only material properties but is also dependent upon physiological and psychological variables as well.

On the basis of weight (lightness), the spunbounded polyethylene among the reusables weighed about one ounce per square yard and the laminate of this invention weighed about three ounces per square yard. Of the other reusables, sample 8 weighed 3.6 ounces per square yard and sample 9 weighed about 6 ounces per square yard.

Figure 4:
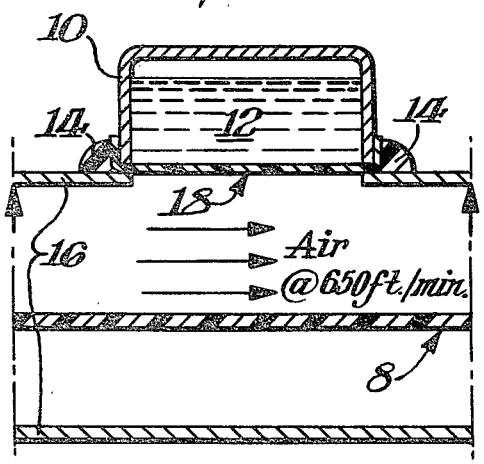
FIG. 4 shows schematically, in cross-section, test apparatus for measuring water vapor transmission rate through a sample of material.

The moisture vapor transmission rate of each sample was measured using apparatus illustrated in FIG. 4. Moisture vapor transmission or breathability is an important factor in that a breathable gown allows perspiration to exit. FIG. 4 shows an inverted cup apparatus in which inverted cup 10 containing water 12 and covered at its open end by a film of expanded PTFE 18 is sealed to a duct 16 through which air passes. The material sample 8 is clamped immediately adjacent film 18 in the air duct. In this way only moisture vapor and not liquid water pass through film 18 and to material sample 8. The decrease in weight of the cup with time provides a measure of the water vapor transmission characteristics of each sample.

Figure 5:
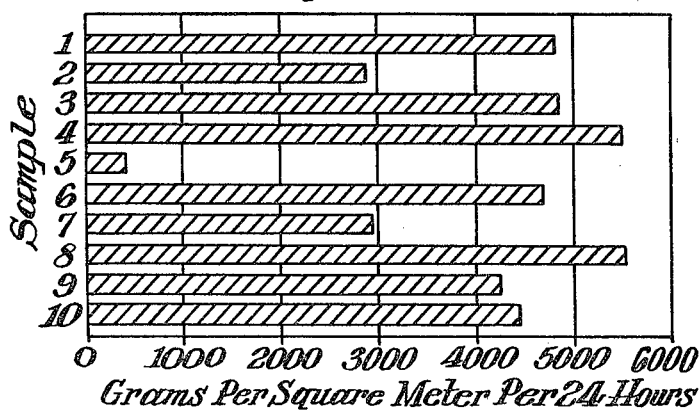
FIG. 5 is a graph showing moisture vapor transmission rate in grams per square meter per day for the same ten samples as in FIG. 2.

FIG. 5 shows the moisture vapor transmission rates for each of the 10 samples discussed above.

Of all 10 samples tested only the laminate of this invention was (a) liquidproof; (b) impervious to bacterial penetration; and (c) comfortable (as reflected by the tests employed).

While the waterproof, bacteria-proof, breathable, and non-glare outer surface, nonlinting and antistatic material of this invention has been described in great detail with reference to hospital gowns and drapes, it will be clear to one skilled in this art that there are many other uses. For example, a black-pigmented laminate would be suitable for use in making black-out tenting.

While the invention has been described in detail in connection with certain examples and preferred embodiments, the foregoing is deemed as illsutrative only of the principles of the invention. Since modifications and changes will readily occur to those skilled in the art, the invention is not to be considered as limited to the exact construction and operation shown and described, and accordingly all suitable modifications and equivalents may be resorted to which fall within the scope of the invention as claimed.

What is claimed is:

1. A flexible layered article suitable for use in hospital gowns and the like, or tents, which permits transfer of water vapor preventing build-up of internal moisture comprising:
    (a) a flexible inner layer of hydrophobic material having a moisture vapor transmission rate exceeding 1000 gms./m$^2$. day and an advancing water contact angle exceeding 90 degrees; and
    (b) a continuous outer hydrophilic layer attached to the outer face of said inner hydrophobic layer, said hydrophilic layer having a moisture vapor transmission rate exceeding 1000 gms./m$^2$. day, said outer hydrophilic layer containing a particulate solid pigment and a liquid antistatic agent dispersed throughout said hydrophilic layer to impart color and antistatic properties to said layered article but not impair its moisture vapor transmission property.

2. The layered article of claim 1 in which a textile layer is attached to the inner face of said hydrophobic layer.

3. The layered article of claim 1 which has a bacterial penetration time above 1000 minutes.

4. The layered article of claim 3 which has a bacterial penetration time above 5000 minutes.

5. The layered article of claim 1 which has a water entry pressure above 20 psig.

6. The layered article of claim 1 which has a moisture vapor transmission rate above 2000 gm./m$^2$. day.

7. The layered article of claim 6 which has a moisture vapor transmission rate above 4000 gm./m$^2$. day.

8. The layered article of claim 1 in which said hydrophobic layer is expanded porous polytetrafluoroethylene that has been heated above its crystalline melt point.

9. The layered article of claim 1 in which said hydrophobic layer is porous polypropylene.

10. The layered article of claim 1 in which said hydrophilic layer is a polyether-polyurethane.

11. The layered article of claim 1 in which said hydrophilic layer is a perfluorosulphonic acid membrane.

* * * * *